(12) United States Patent
Tkachuk

(10) Patent No.: US 7,796,265 B2
(45) Date of Patent: Sep. 14, 2010

(54) OPTICAL ABSORPTION GAS ANALYSER

(75) Inventor: Michael Tkachuk, Sayville, NY (US)

(73) Assignee: BAH Holdings LLC, Glen Cove, NY (US)

( * ) Notice: Subject to any disclaimer, the term of this patent is extended or adjusted under 35 U.S.C. 154(b) by 324 days.

(21) Appl. No.: 12/109,254

(22) Filed: Apr. 24, 2008

(65) Prior Publication Data

US 2009/0268204 A1    Oct. 29, 2009

(51) Int. Cl.
    *G01N 21/00*    (2006.01)
(52) U.S. Cl. ...................................... 356/437
(58) Field of Classification Search ................ 356/437
    See application file for complete search history.

(56) References Cited

U.S. PATENT DOCUMENTS

| | | | |
|---|---|---|---|
| 4,736,103 A | 4/1988 | Nelson et al. | |
| 4,885,469 A | 12/1989 | Yamagishi et al. | |
| 5,696,586 A | 12/1997 | Ivanov | |
| 6,147,351 A * | 11/2000 | Huiku | 250/343 |
| 6,956,648 B2 | 10/2005 | Loicht et al. | |
| 7,063,667 B1 | 6/2006 | Oren et al. | |
| 2003/0090670 A1 | 5/2003 | Capetanopoulos | |

FOREIGN PATENT DOCUMENTS

| | | |
|---|---|---|
| EP | 0 359 213 | 3/1990 |
| EP | 0 396 319 | 11/1990 |
| WO | WO 01-40748 | 6/2001 |
| WO | WO 01-65219 | 9/2001 |

OTHER PUBLICATIONS

Unpublished co-pending U.S. Appl. No. 11/670,280, filed Feb. 1, 2007 (which is not being furnished herewith, pursuant to the Commissioner's Notice dated Sep. 21, 2004).
Search report for PCT Application GB/01/00711.
Search report for PCT Application GB/00/04523.

* cited by examiner

*Primary Examiner*—Roy Punnoose
(74) *Attorney, Agent, or Firm*—James P. Muraff; Neal, Gerber & Eisenberg LLP

(57) ABSTRACT

An optical absorption gas analyzer for determining the concentration of a target gas in a sample is disclosed. The analyzer comprises a chamber for containing the sample in use; a radiation source assembly arranged to emit radiation into the chamber; a first radiation detector assembly arranged to detect radiation transmitted along a first optical path through the chamber and a second radiation detector assembly arranged to detect radiation transmitted along a second optical path through the chamber, wherein the length of the second optical path which the sample can intercept is shorter than that of the first optical path. The analyzer further comprises a processor adapted to generate a sensing signal $S_S$ based on the detected radiation transmitted along the first optical path and a reference signal $S_R$ based on the detected radiation transmitted along the second optical path. The processor determines the concentration of the target gas in the sample based on a comparison of the sensing signal with the reference signal.

45 Claims, 3 Drawing Sheets

OPTICAL ABSORPTION GAS ANALYSER

CROSS-REFERENCE TO RELATED APPLICATIONS

None.

TECHNICAL FIELD

This invention relates to an improved instrument for the measurement of concentration of a target gas by means of optical absorption. In particular, the invention relates to apparatus and methods for non-dispersive infrared (NDIR) measurement based on the absorption of radiation by the gas of interest.

BACKGROUND AND SUMMARY OF THE INVENTION

Optical absorption techniques such as non-dispersive infrared (NDIR) measurement have been recognized for many years as sensitive, stable and reliable methods of gas concentration measurement. In a typical NDIR method, the selective absorption of infrared radiation by certain gas species of interest is measured to determine the concentration of the target gas in a sample. This has a wide variety of applications—for example, NDIR measurements detecting absorption of radiation by carbon dioxide and other gases, such as carbon monoxide or hydrocarbons, are commonly used to monitor atmospheric composition or automotive exhaust, as well as in fire detectors.

A conventional NDIR instrument typically comprises the following elements:

a source of radiation (usually infrared), such as an incandescent lamp or another electrically heated element that serves as a blackbody emitter, e.g. a silicon carbide rod or nichrome filament;

a narrow bandwidth interference filter arranged to ensure that only radiation absorbed by gas of interest is measured;

a gas chamber for containing a sample including the target gas of interest; and a photodetector for detecting radiation transmitted by the sample and transforming the intensity of the detected radiation into an electrical signal.

Often, the intensity of incident radiation may be modulated by a mechanical chopper or by an electrically modulated radiation source ("on and off" regime).

Such a device is termed a "one channel" NDIR sensor and represents the most basic NDIR device. This type of instrument is relatively inexpensive, but does not provide any kind of compensation for instrument drift over time which may occur due to the radiation source and/or the photodetector ageing, or accumulation of dirt and dust in the optical path, for example. As a result, "one channel" NDIR instruments need to be calibrated relatively often.

"Two channel" NDIR sensors have a signal channel and a reference channel. The signal channel operates in exactly the same way as the "one channel" device describes above, with the wavelength of the band pass filter adjusted to the absorption wavelength(s) of the gas of interest.

The reference channel usually works in another wavelength band, at which the target gas species does not absorb. This provides a base line for the signal channel. The differential signal between the signal and reference channels, normalized on reference channel intensity, gives an absorption signal which is stable with respect to any intensity drift resulting from the radiation source (or detector). In typical "two channel" sensors, the source of radiation has a wide spectral output, comprising both the signal and reference wavelengths. Another type of "two channel" NDIR sensor comprises two photodetectors and includes two separate gas cells into which the emission from the radiation source is split along paths of equal lengths. One cell is filled with non-absorptive (inert) gas to provide a reference channel, and the other with the sample gas (including the gas of interest). Such sensors can work with good stability with the two channels working on the same wavelength (corresponding to an absorption line of the target gas), but the requirement for a separate, sealed gas reference cell containing an inert gas is a serious limitation in a portable, low cost design.

As a result, the use of a reference channel working on a wavelength where the target gas does not absorb is preferred in two channel NDIR instruments and has been found to provide a high degree of compensation of source radiation drift, and thus good measurement accuracy. Practically all such devices use an incandescent bulb as the source of radiation since it provides the necessary wide wavelength radiation band. However, such radiation sources are slow (typically, the response time is more than 100 milliseconds) and has significant power consumption (200 milliwatts or more). As such, these components are not suitable for portable, low power sensors which can typically support a power consumption of no more than 1-2 milliwatts.

Radiation sources such as light emitting diodes (LEDs), instead, are very fast (the response time is of the order of a few microseconds) and can be used in regimes having a power consumption of less than one milliwatt. However, LEDs suffer from the problem that their output power and emitted radiation wavelength depend significantly on temperature. These temperature dependences have a fundamental nature and can not be avoided in the design of the LED.

Another problem encountered in the use of LEDs, as compared with bulbs, is the relatively narrow wavelength range of emission (usually not exceeding one micrometer). As a result, an LED cannot be used the same way as a bulb in a conventional NDIR sensor, since it cannot provide emission on a reference wavelength (in addition to the absorption wavelength). Using a second LED to provide the reference wavelength does not assist, because for LEDs working on different wavelengths, the temperature dependences of parameters (intensity and wavelength of emission) are different and cannot be precisely compensated.

In accordance with the present invention, an optical absorption gas analyser for determining the concentration of a target gas in a sample, comprises:

a chamber for containing the sample in use;

a radiation source assembly arranged to emit radiation into the chamber;

a first radiation detector assembly arranged to detect radiation transmitted along a first optical path through the chamber;

a second radiation detector assembly arranged to detect radiation transmitted along a second optical path through the chamber, wherein the length of the second optical path which the sample can intercept is shorter than that of the first optical path; and a processor adapted to generate a sensing signal $S_S$ based on the detected radiation transmitted along the first optical path and a reference signal $S_R$ based on the detected radiation transmitted along the second optical path, and to determine the concentration of the target gas in the sample based on a comparison of the sensing signal with the reference signal.

By arranging for radiation to be detected along a second optical path which is shorter than the first, the invention provides a reference channel which operates using the same radiation as the signal channel, yet does not require the provision of a separate (inert) cell, since both paths pass through the same chamber. The relatively short length of the second optical path with which the sample can interact (compared with that of the first optical path) means that absorption in the reference channel is suppressed and can be used to accurately compensate for drift. Preferably, the length of the second optical path with which the sample can interact is made as short as possible, and in any case significantly shorter than that of the first optical path. As a result any losses caused by absorption in the reference path will be small.

This arrangement makes it possible to use an LED or other fast-response radiation source since both the signal and reference channels can operate at the same (or overlapping) waveband.

It is of key importance that, within the chamber, the length of the second optical path which the sample can intercept (i.e. to which the sample has access) is shorter than that of the first optical path, however in certain embodiments it is preferred that the entire length of the first optical path (i.e. from source to detector) is greater than that of the second.

Preferably, the generated sensing signal $S_S$ depends upon the concentration of the target gas in the sample and on the intensity of radiation emitted by the radiation source assembly.

Preferably, the generated reference signal $S_R$ depends upon the intensity of radiation emitted by the radiation source assembly, and is substantially independent of the concentration of the target gas in the sample. This is achieved by arranging the length of the second optical path with which the sample can interact to be as short as possible.

Advantageously, the processor is adapted to determine the concentration of the target gas in the sample by generating a differential absorption signal $S_A$ corresponding to the difference between the sensing signal $S_S$ and the reference signal $S_R$:

$$S_A = S_S - S_R$$

In this way, the output signal takes account of any variation in the radiation emitted by the source.

Preferably, the processor is further adapted to generate a normalised differential absorption signal $S_N$ relative to the reference signal $S_R$:

$$S_N = S_A / S_R$$

This provides a dimensionless output which is dependent on target gas concentration but not the intensity of the source radiation and is also independent of perturbations in the emitted radiation wavelengths caused by temperature variations.

The source and detectors could be arranged at various opposing sides of the chamber, making use of different dimensions of the chamber to define the first and second optical paths. However, in preferred embodiments, at least one optical guiding assembly is disposed within the chamber to define at least one of the first and second optical paths. This can be used to maximise the length of the first optical path, and minimise that of the second.

Any suitable optical elements could be used to construct the optical guiding assembly, including, if desired, parts of the chamber wall itself. Advantageously, the optical guiding assembly comprises a partially-reflective element arranged to split the first optical path from the second, preferably a partially-reflective mirror or a partially-reflective prism. Such an element could, for example, make use of a semi-silvered mirror. However, preferably, the partially-reflective element comprises a mirror surface having one or more non-reflective regions through which the first or second optical path passes.

In a particularly preferred embodiment, the optical guiding assembly comprises a first mirror having a transmissive portion, the first mirror being arranged to receive radiation emitted by the radiation source assembly and to transmit a portion of the radiation through the transmissive portion to the second detector assembly, and a second mirror arranged to receive radiation reflected by the first mirror and reflect it towards the first detector assembly through the transmissive portion of the first mirror. This has been found to provide a particularly compact means of achieving a long first path and short second path within the chamber. Preferably, the first and/or second mirrors have a shape arranged to focus incident radiation, preferably spherical or parabolic.

In other preferred examples, the optical guiding assembly comprises a reflective element arranged to intercept a portion of the radiation emitted by the radiation source assembly, preferably a mirror, a reflective portion of the chamber's interior or an optical fibre. In such cases, only part of the radiation emitted by the source is incident on the reflective element, the remainder continuing past the element on the other of the two optical paths.

The optical guiding assembly inside the sample chamber may comprise solely reflective surfaces, such as mirrors, in which case the whole of the first and/or second optical path can be intercepted by the sample in the chamber. In other cases, one or more optical components may take the form of radiation-transparent elements (e.g. prisms or optical fibres), within which the optical path cannot interact with the sample. In one preferred embodiment, the second optical path is substantially wholly contained within one or more optical elements making up the optical guiding assembly. In this way, absorptions on the reference channel can be eliminated entirely.

As indicated above, preferably the first optical path should be significantly longer than the second. Advantageously, the length of the first optical path which the sample can intercept is at least 3 times that of the second optical path, preferably more than 5 times the length and still preferably more than 8 times the length.

Preferably, the length of the second optical path which the sample can intercept is less than or equal to 40 mm, preferably less than or equal to 20 mm, still preferably less than or equal to 10 mm.

The arrangement is particularly advantageous when implemented using a radiation source assembly comprising a narrow band emitter adapted to emit radiation over a waveband corresponding to an absorption wavelength of the target gas. Preferably, the width of the waveband emitted by the radiation source assembly is less than or equal to 1 micron. In certain cases, the radiation source assembly may additionally comprise a filter for controlling the waveband emitted. Advantageously, the filter is an interference filter.

It is especially preferred that the radiation source assembly comprises an emitter having a response time of less than or equal to 100 milliseconds, preferably less than 1 millisecond, still preferably less than 50 microseconds.

In preferred embodiments, the radiation source assembly comprises a LED. Advantageously, the radiation is infrared radiation.

Preferably, the first and second detector assemblies are adapted to detect radiation of the same wavelength(s) as each other, corresponding to an absorption wavelength of the target gas. This ensures that the compensation made using the reference channel is most accurate. In certain embodiments, the first and second detector assemblies each comprise a filter for controlling the wavelength(s) of radiation detected. Advantageously, the first and second detector assemblies each comprise a photodetector, preferably a photodiode, a pyroelectric photodetector or a thermocouple photodetector.

Preferably, the optical absorption gas analyser further comprises a controller adapted to control power supplied to the radiation source assembly. In particularly preferred embodiments, the controller is adapted to perform pulse width modulation control, supplying the radiation source assembly with discrete pulses of power. This enables the source to be controlled in particularly low power consumption regimes. Advantageously, the pulses have a duration of between 15 microseconds and 100 milliseconds, preferably approximately 20 microseconds. The pulse width modulated signal may have a period of between 100 microseconds and 10 seconds. The pulse width modulated signal advantageously has a duty cycle of between 0.01% and 50%, preferably approximately 0.04% to 0.8%.

The analyser could be connected to an external power source in order to supply power to the radiation source and processing components. However, it is preferred that that the analyser further comprises a power source so that the device is fully portable. Preferably the power source comprises a battery, solar cell or solar-powered battery. In particularly preferred embodiments, a highly efficient solar battery (up to 28% efficient) is provided, which can deliver several milliwatts of energy even in low illumination, significantly economising on battery power.

As noted previously, certain radiation source types have a significant dependence on temperature. The same is true for certain types of radiation detector, in particular semiconductor photodetectors. Therefore, preferably, the first and second detector assemblies are located adjacent one another, preferably arranged on the same or adjacent faces of the chamber. This keeps temperature discrepancies due to position of the elements to a minimum.

To alleviate this problem still further, the first and second detector assemblies are preferably arranged in thermal contact with one another. This may be achieved, for example, by mounting both detectors on a thermally conductive plate. In other embodiments, a thermal conductor may be connected between the first and second detector assemblies.

Preferably, the chamber is provided with at least one aperture for gas ingress from the surrounding atmosphere. This enables an atmosphere to be monitored in real time. However, in alternative situations, the sample could be input to the chamber by an operator for evaluation.

A further problem that may be encountered is high humidity environments which can lead to water condensation inside the chamber. If this occurs on optical surfaces, the water droplets will cause absorption of radiation as well as scattering, distorting the measurements obtained from the instrument. Therefore, preferably, the optical absorption gas analyser further comprises a condensation preventor for preventing the condensation of water on optical surfaces forming part of the first and/or second optical paths. This could take active or passive forms. In one embodiment, the condensation preventor comprises a thermal isolator arranged to thermally isolate each optical surface. Preferably, the thermal isolator forms a substrate upon which the optical surface is supported, preferably a mirror surface. Advantageously, the thermal isolator is formed of a material with low thermal capacity and low thermal conductivity, preferably a polymer, still preferably a polymer foam. Examples of suitable materials include (expanded) polyisocyanurate, eg Trymer™ 1800, and Primaplex™.

In other examples, the condensation preventor preferably comprises a heater arranged to heat each optical surface. Preferably, the optical surface comprises a conductive material and is provided with connectors for connection to a power supply to thereby form a heating element. The optical absorption gas analyser preferably further comprises a controller for controlling power supply to the heating element. Advantageously, the optical surface is reflective and comprises a metallic material, preferably aluminium, silver or gold.

BRIEF DESCRIPTION OF THE DRAWINGS

Examples of optical absorption gas analysers in accordance with the invention will be described below with reference to the accompanying drawings, in which.

DETAILED DESCRIPTION

Figure 1:
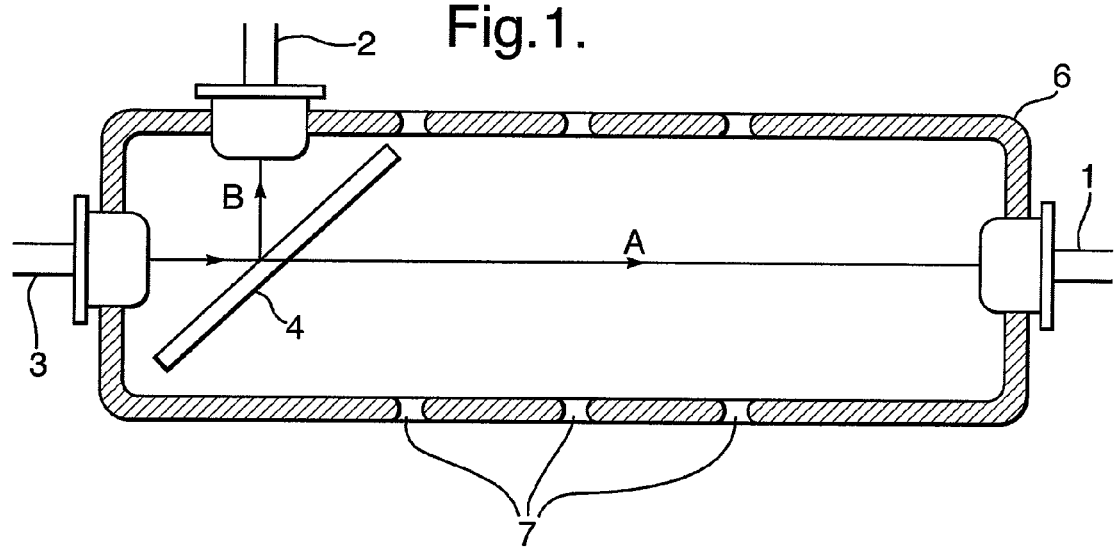
FIG. 1 depicts a first embodiment of an optical absorption gas analyser.

The first embodiment, shown in FIG. 1, implements a simple, linear design. An elongate chamber 6 is provided for containing a gas sample in use. In this example, the chamber 6 has a number of apertures 7 for gas ingress, which enables fluid communication between the interior of the chamber 6 and the surrounding atmosphere. A radiation source 3, in this case an InGaAs, PbS, or PbSe-based LED, is arranged at one end of the chamber 6 and is opposed by a first radiation detector 1, such as a photovoltaic detector, at the far end of the chamber 6. Radiation emitted by source 3 passes through the chamber 6 on a first optical path A to reach the first detector 1.

A light guiding assembly comprising a partially-reflective element in the form of semi-silvered mirror 4 is disposed between the radiation source 3 and the first detector 1 so as to intercept the radiation emitted by the source 3. Part of the radiation passes through the semi-silvered mirror 4 to continue on the first optical path A toward the first detector 1. The other part of the radiation incident on mirror 4 is reflected onto a second optical path B towards a second detector 2.

The radiation source 3 is arranged to emit a narrow waveband of radiation in the IR spectrum, which aligns with an absorption wavelength of the target gas to be measured. For example, in the detection of methane, the waveband of emitted radiation will be around 3.2 to 3.5 microns. Both detectors 1 and 2 are also arranged to detect the same (or overlapping) waveband as that emitted by the source. By arranging the signal and reference channels to work on the same wavelength precise thermal equivalency of the signal and reference photodetectors' response is provided.

As shown in FIG. 1, the semi-silvered mirror 4 is arranged adjacent the radiation source 3, such that the second optical path B is short. In practice, the semi-silvered mirror 4 will be arranged as close as possible to the source 3 in order to minimise the length of optical path B. In this case, the first optical path A is approximately 3-4 times the length of the second optical path B. The relatively short length of the second optical path means that there is little interaction with the sample contained in the chamber 6 and, consequently, minimal absorption of radiation.

The first detector 1 outputs a sensing signal $S_S$, which is dependent on the concentration of the target gas in the sample, as well as any variation in the intensity of emitted radiation and/or the detector performance. The second detector 2 outputs a reference signal $S_R$, which depends on emitted radiation intensity and detector performance, but is largely independent of the target gas concentration due to its short length.

The signals from the detectors 1 and 2 are output to a processor (not shown in FIG. 1), which compares the sensing signal $S_S$ with the reference signal $S_R$ to generate an output representative of the concentration of the target gas in the sample in which variations in the performance of the radiation source and detectors have been corrected. In this particular example, the processor generates a differential absorption signal, $S_A$ from the difference between the sensing and reference channels:

$$S_A = S_S - S_R$$

The differential signal is then normalised based on the reference intensity to obtain a measurement value which is independent of the emitted intensity:

$$S_N = S_A / S_R$$

This value can be converted to a concentration measurement using look-up tables or a calibrated graph, for example.

Thus, the embodiment uses the same radiation from one IR LED (for example) in the reference channel (path B) that is used in the signal channel (path A) without any need for a reference gas cell. In this case the working emission wavelength for the reference channel is in a region of target gas absorption and special arrangements for differential measurement of absorption signal are provided. Namely, the value of the differential absorption signal of gas of interest $S_A$ will be maximal if there is no absorption in the reference channel, so to suppress absorption in the reference channel, the optical path B between the source of radiation and the second detector 2 is made as short as possible. Provided the second optical path B is much shorter than signal channel path A, the losses in the differential signal caused by absorption in the reference channel will be low.

The use of an LED in the embodiment provides further particular advantages due to its fast response time. A controller (not shown in FIG. 1) is provided to control supplied power to the radiation source 3 in a pulse modulated regime. This makes it possible to significantly reduce the power consumed by the instrument without affecting its sensitivity. The controller preferably supplies short current pulses of controlled amplitude to the source 3 having a pulse duration of around 20 microseconds and a duty cycle of about 1/2500 (0.04%) on any convenient frequency. The pulse duration and period (time between the start of each pulse) can be adjusted to suit the intended application. For example, in fast-changing environments it may be preferred to have relatively fast sampling using a signal period of around 100 microseconds. To keep the duty cycle (and hence the power consumption) reasonably low, the pulse duration should also be short: 15 microseconds has been found acceptable, giving a duty cycle of 15%. In other circumstances, where relatively slow changes in the atmosphere are likely to be encountered, a less frequent measurement cycle may be acceptable, allowing the power consumption to be reduced still further. For example, sampling at 10 second intervals (=signal period) may be appropriate and in such a case, the pulse duration can be significantly longer (e.g. up to 100 milliseconds) whilst retaining a very low duty cycle (e.g. 1%).

Narrow band gap semiconductor (InGaAs, PbS, PbSe)-based LEDs and photodetectors, are preferred since they have a very fast response time of the order of 5-10 microseconds.

The analyzer includes a power source (not shown in FIG. 1), such as a battery or, preferably, a solar battery for supplying power to the components. Recent improvements in solar batteries have lead to high efficiency, which can deliver several milliwatts of power even in low illumination. For example, a suitable solar cell is the Ultra Triple Junction (UTJ) solar cell made by Spectralab Inc. of California, USA, which can achieve 28.3% efficiency, which is 5-6 times more than conventional solar batteries.

In order to improve the accuracy of the instrument still further, good thermal contact between temperature-sensitive semiconductor components (the source and detectors) is advantageous to prevent any distortion between the signal and reference channels when temperature is varied. The sensitivity of the fast IR semiconductor photodetectors depends on temperature with a coefficient of about 0.5% per Celsius degree. Hence in order to achieve maximal accuracy of measurement of the differential signal $S_A$, the difference in temperature of the two detectors should be minimal.

The general trend here should be to dispose the photodetectors 1 and 2 close to each other as much as is possible. So, the first embodiment is not perfect from this point of view, because the photodetectors 1 and 2 are placed on different sides of the gas chamber 6 at a distance from one another which is similar to the first optical path A.

Figure 2:
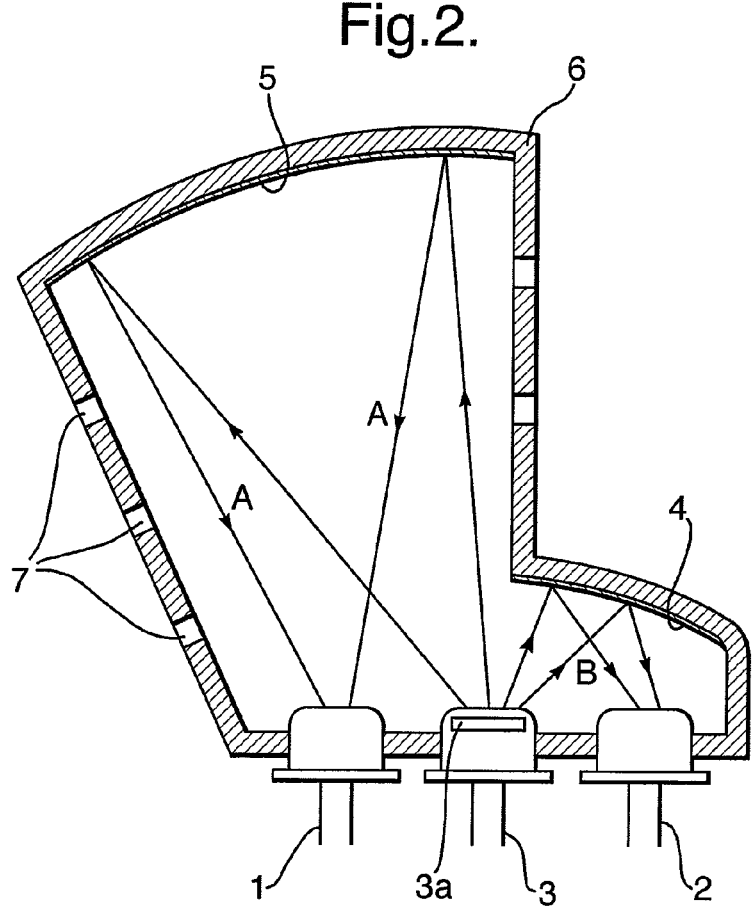
FIG. 2 depicts a second embodiment of an optical absorption gas analyser.

A second embodiment, shown in FIG. 2 (components equivalent to those in FIG. 1 retain the same reference numerals), is much improved in this sense, because photodetectors 1 and 2 are disposed close to one another, and on the same surface of the chamber 6.

This compact, temperature-stable design uses a light guiding assembly in the form of reflective mirrors 4 and 5. The chamber 6 is shaped so as to support a first mirror 4 close to the radiation source 3. The mirror intercepts only a portion of the radiation emitted by the source 3 and reflects it towards a photodetector 2 along a short optical path B. Radiation not intercepted by the first mirror 4 crosses a wide portion of the chamber 6 where it is reflected by a second mirror 5 towards another detector 1 along a longer optical path A. The long optical path A constitutes the sensing channel, and the short optical path B represents the reference channel.

The mirror elements 4 and 5 may comprise mirrors affixed to the chamber walls or could be formed by reflective surfaces provided on the internal chamber wall itself.

In this case, the radiation source 3 includes a filter 3a for controlling the emitted waveband to the absorption wavelength of the target gas. In other cases, the filter could be provided on each of the detectors 1 and 2. The filter 3a is preferably an interference filter.

Power to the radiation source 3 is conveniently managed in a pulse modulated regime using a controller as described in the first embodiment. A power source such as a solar battery may also be included as previously described.

The signals from the first and second detectors 1 and 2 are processed as described in the first embodiment to output a signal representing the concentration of the target gas in the sample, corrected to remove any distortion caused by source drift.

Figure 3:
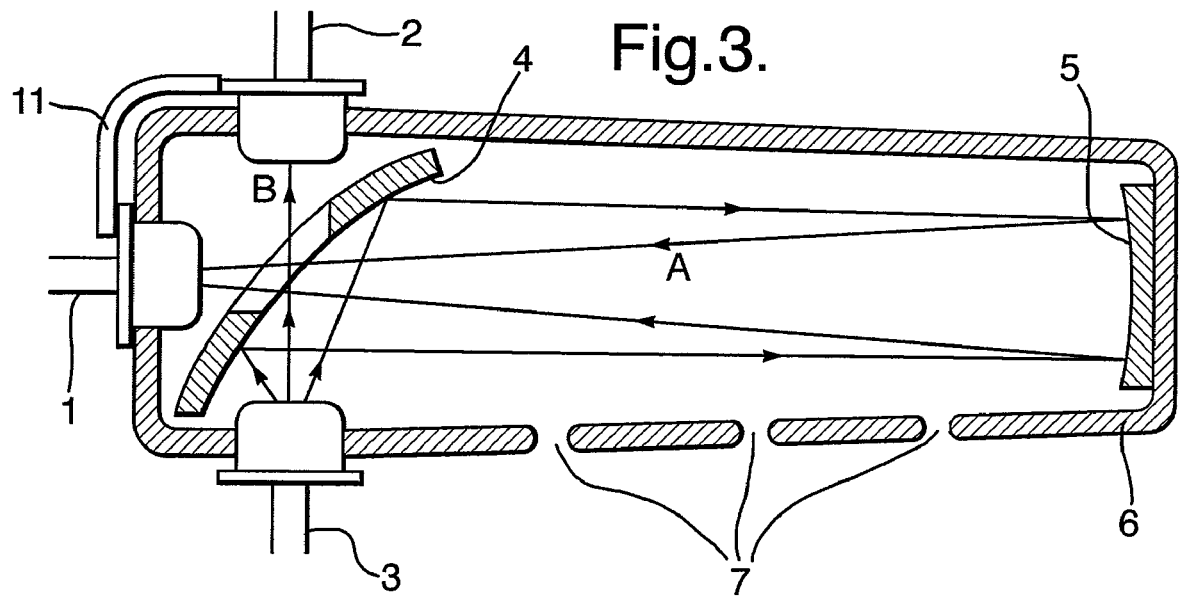
FIG. 3 depicts a third embodiment of an optical absorption gas analyser.

A third embodiment shown in FIG. 3, improves the temperature accuracy still further by the use of a thermal conductor 11 connecting the first and second detectors 1 and 2. In this way the photodetectors will have good thermal contact, leading them to remain in thermal equilibrium and maintain the same temperature as each other with a good accuracy.

The third embodiment makes use of a light guiding assembly comprising a partially reflective mirror 4 arranged adjacent the radiation source 3. As in the case of the second embodiment, the radiation source 3 may include a filter (not shown), such as a narrow bandwidth interference filter, adjusted to pass a radiation waveband corresponding to (at least including) an absorption line of the target gas. The reflected portion of the radiation is directed towards a mirror 5 arranged at the far end of the elongate chamber 6. The radiation is reflected back towards a first detector 1, passing through a transparent window in the partially reflective mirror 4 to reach it along long optical path A. The other part of the radiation initially incident on partially reflective mirror 4 also strikes the transparent window and passes directly to a detector 2 along a short optical path B. The mirrors 4 and 5 are shaped so as to "collect" or focus incident radiation, as depicted in FIG. 3. In this particular case each mirror is spherical although parabolic or other mirror shapes may be required in other implementations.

The thermal conductor 11 may take the form of a plate to which both detectors 1 and 2 are mounted, or could be an additional component attached to each. The component is preferably made from a material with high thermal conductivity, such as a metal or alloy.

The third embodiment employs a controller (not shown) as in the case of the first embodiment to pulse modulate power supplied to the radiation source, and a suitable power source such as a high-efficiency solar battery. Similarly, a processor generates a measurement signal based on the sensed and reference signals as set out in relation to the first embodiment.

In each of the above embodiments, the optical elements making up the optical guiding assembly inside the chamber 6 comprise reflective or partially reflective surfaces 4, 5. As such, the entire length of each optical path A, B (defined from the radiation source 3 to the respective detector 1 or 2) can be intersected by the sample contained in the chamber 6.

However, in some cases it may be preferable to include optical elements which are transparent yet impervious to the sample gas. The gas is thereby prevented from interacting with the portion of the optical path contained within the element. This can advantageously be used to shorten still further the length of the second optical path B which can be intersected by the target gas species, so reducing the occurrence of absorption on the reference channel.

Figure 4A:
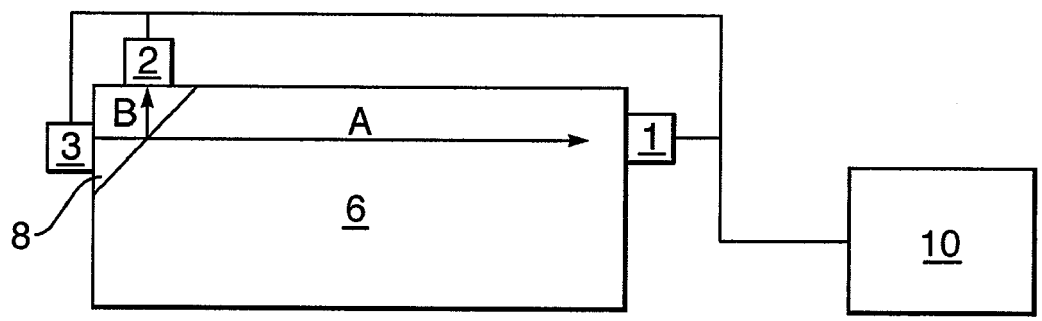
FIGS. 4a and 4b schematically show fourth and fifth embodiments of an optical absorption gas analyser.

FIG. 4a shows schematically a fourth embodiment of an optical absorption gas analyzer in which a partially-reflective prism 8 is disposed inside chamber 6 adjacent radiation source 3 and detector 2. Radiation emitted by source 3 passes directly into the prism 8. On striking the prism's angled surface, part of the radiation is transmitted and continues on a first optical path A towards another detector 1, constituting the sensing channel. The other portion of the radiation is reflected with prism 8 towards detector 2 along a shorter, second optical path B, forming the reference channel. Since the whole of path B is contained within prism 8, the target gas has no opportunity to interact with the radiation, and there is no absorption on the reference channel. A processor 10 is provided to generate a measurement signal from both channels as described above. Processor 10 may also incorporate a controller for controlling the power supplied to the radiation source as in the above embodiments, and a power source such as a solar battery.

Figure 4B:
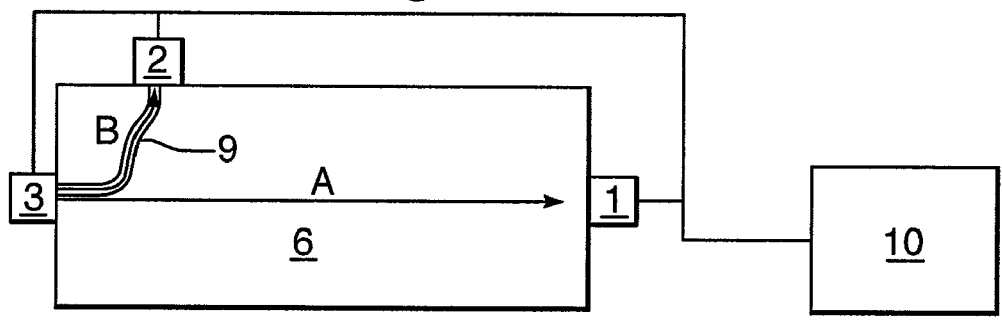

A fifth embodiment is depicted in FIG. 4b, which is identical to the fourth embodiment, save for the provision of an optical fibre 9 in place of prism 8. The optical fibre is arranged to receive a portion of the radiation emitted by source 3 and direct it, through the chamber 6, to detector 2. The optical fibre 9 constitutes optical path B. The remaining radiation which is not incident on fibre 9 passes on optical path A to detector 1. Since the whole of path B is contained within optical fibre 9, as in the FIG. 4a embodiment, there is no absorption on the reference channel.

Components such as prism 8 and optical fibre 9 can also be used in conjunction with other optical elements and spaced from the walls of chamber 6 to decrease (but not eliminate entirely) the "open" length of the second optical path B. Likewise it will be appreciated that such components can be used to implement the arrangements described in any of the above embodiments, including those shown in FIGS. 2 and 3 hereto. For example, in the third embodiment, shown in FIG. 3, the partially-transparent mirror 4 could be implemented using a partially-silvered prism having a suitable curved reflective surface, thereby shortening still further the length of the second optical path with which the sample can interact.

Instruments such as those described in the above embodiments are suitable for use in a wide range of applications, including personal safety devices such as a methane concentration monitor which is worn by a user in environments where there is a risk of exposure to the target gas. Such devices should be capable of use across a wide range of temperature and humidity, including relative humidity of close to 100%. Safety requirements require that the monitor must remain operational even if there exists the possibility of water condensation due to the high level of humidity.

The most significant problems occur when the monitor moves from a cold environment into the warm. On contact with warm air, the cold optical parts (such as mirrors 4 and 5) inside the instrument could cool the air in the chamber 6 below dew point and cause water to condense on the optical parts of the chamber. Water on the optical surfaces will cause absorption and scattering of IR radiation and the instrument will lose sensitivity to the target gas, which is not permissible in a safety device. To prevent this, the instruments described in the above embodiments are preferably provided with a condensation preventor.

The system for preventing water condensation could be passive or active. Active systems use additional energy from a power supply, whereas passive systems do not. For small portable low power device a passive system may therefore be preferred.

Figure 5A:
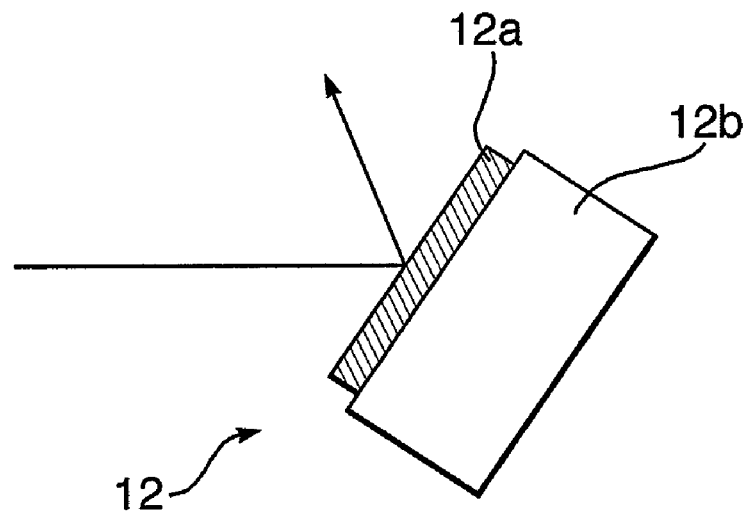
FIGS. 5a and 5b show two examples of condensation preventors suitable for use in the above embodiments.

An example of a passive condensation preventor 12 is shown in FIG. 5a. Passive systems are based on the thermodynamic balance of energy exchange which occurs when optical parts of the device are transferred from one temperature to another.

For prevention of condensation it is necessary to achieve the minimal temperature difference between the optical parts and ambient temperature during any thermal transition. This will determine the process of energy exchange and thermal equilibrium achievement. The goal here is to heat the optical surfaces 12a (e.g. mirrors 4 and 5) before the gas near the mirror reaches the dew point temperature. By forming the substrate 12b upon which the mirror surface 12a is supported from a material with a low thermal capacity and low thermal conductivity (polymer foam, Trymer™ 1800 or Primaplex™, for example), the working surface 12a of the mirror will be thermally isolated from the substrate 12b, and the energy of the gas inside the gas chamber 6 will be enough to warm up the optical surface 12a to a temperature close to that of the gas inside the chamber 6, thereby preventing condensation of water inside the gas chamber 6.

For example, in the case of a device with a gas chamber volume of 10 $cm^3$, the reserve of the thermal energy of the gas inside the chamber is 13 mJ when the temperature changes by 1 degree Celsius. This is the amount of energy that can be obtained from the gas for heating of the cold optical parts.

For a mirror with a plastic substrate 12b (thermal capacitance approx. 1.65 J/gram per degree Celsius, thermal conductivity approx. 0.033 W/m per degree Celsius, density 28.8 kg/m$^3$) of dimensions 1 cm$^2$ by 0.5 mm deep, heating of the mirror and the volume of the substrate adjacent the mirror requires 1.8 mJ per 1 degree Celsius.

This means that inside the gas chamber there is enough energy to keep a difference of less than 1 degree Celsius between the optical surface of the mirror 4, 5 and the ambient air if the optical surface 12a is thermally isolated enough by the substrate volume 12b. It is necessary to note here that, if the temperature difference between ambient air (outside the chamber 6) and the device optics is significant (e.g. ten degrees Celsius), it is important to have a good exchange of the air inside and outside the chamber 6.

In some cases, it may be desirable to supplement the passive system of condensation prevention with an active system, or to use an active system in place of the passive system. An active system uses additional power for heating of the optical parts 4, 5.

Figure 5B:
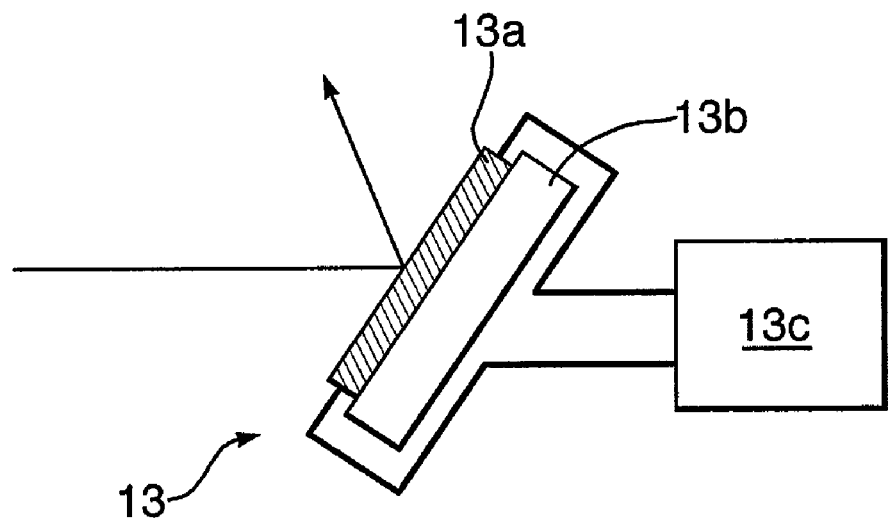

A particularly convenient active system 13 is shown in FIG. 5b, in which the metalized surface of the mirror 13a is used as a resistive heater. The mirror surface 13a on substrate 13b (which may be insulating as in FIG. 5a) is connected to a power supply 13c, which may form part of processor 10. As shown above, the required energy is about 10 mJ per degree. A power of about ten milliwatts is enough for heating the mirror 13a by one degree per second. An aluminum mirror (with area 1 cm$^2$ and thickness 0.2 micron) has a resistance of about 140 ohms, so applying one volt over several seconds should prevent the water condensation. The mirror surface could alternatively be made from another suitable conductive material such as silver, gold or another metal, or could have a heating filament arranged in or behind the surface.

What is claimed is:

1. An optical absorption gas analyser for determining the concentration of a target gas in a sample, comprising:
   a chamber for containing the sample in use;
   a radiation source assembly arranged to emit radiation into the chamber;
   a first radiation detector assembly arranged to detect radiation transmitted along a first optical path through the chamber;
   a second radiation detector assembly arranged to detect radiation transmitted along a second optical path through the chamber, wherein the length of the second optical path which the sample can intercept is shorter than that of the first optical path; and
   a processor adapted to generate a sensing signal $S_S$ based on the detected radiation transmitted along the first optical path and a reference signal $S_R$ based on the detected radiation transmitted along the second optical path, and to determine the concentration of the target gas in the sample based on a comparison of the sensing signal with the reference signal.

2. An optical absorption gas analyser according to claim 1, wherein the entire length of the first optical path is greater than that of the second.

3. An optical absorption gas analyser according to claim 1, wherein the generated sensing signal $S_S$ depends upon the concentration of the target gas in the sample and on the intensity of radiation emitted by the radiation source assembly.

4. An optical absorption gas analyser according to claim 1, wherein the generated reference signal $S_R$ depends upon the intensity of radiation emitted by the radiation source assembly, and is substantially independent of the concentration of the target gas in the sample.

5. An optical absorption gas analyser according to claim 1, wherein the processor is adapted to determine the concentration of the target gas in the sample by generating a differential absorption signal $S_A$ corresponding to the difference between the sensing signal $S_S$ and the reference signal $S_R$:

$$S_A = S_S - S_R.$$

6. An optical absorption gas analyser according to claim 5, wherein the processor is further adapted to generate a normalised differential absorption signal $S_N$ relative to the reference signal $S_R$:

$$S_N = S_A / S_R.$$

7. An optical absorption gas analyser according to claim 1, wherein at least one optical guiding assembly is disposed within the chamber to define at least one of the first and second optical paths.

8. An optical absorption gas analyser according to claim 7 wherein the optical guiding assembly comprises a partially-reflective element arranged to split the first optical path from the second, preferably a partially-reflective mirror or a partially-reflective prism.

9. An optical absorption gas analyser according to claim 8 wherein the partially-reflective element comprises a mirror surface having one or more non-reflective regions through which the first or second optical path passes.

10. An optical absorption gas analyser according to claim 7 wherein the optical guiding assembly comprises a first mirror having a transmissive portion, the first mirror being arranged to receive radiation emitted by the radiation source assembly and to transmit a portion of the radiation through the transmissive portion to the second detector assembly, and a second mirror arranged to receive radiation reflected by the first mirror and reflect it towards the first detector assembly through the transmissive portion of the first mirror.

11. An optical absorption gas analyser according to claim 10 wherein the first and/or second mirrors have a shape arranged to focus incident radiation, preferably spherical or parabolic.

12. An optical absorption gas analyser according to claim 7 wherein the optical guiding assembly comprises a reflective element arranged to intercept a portion of the radiation emitted by the radiation source assembly, preferably a mirror, a reflective portion of the chamber's interior or an optical fibre.

13. An optical absorption gas analyser according to claim 7 wherein the second optical path is substantially wholly contained within one or more optical elements making up the optical guiding assembly.

14. An optical absorption gas analyser according to claim 13 wherein the one or more optical elements comprise prisms or optical fibres.

15. An optical absorption gas analyser according to claim 1 wherein the length of the first optical path which the sample can intercept is at least 3 times that of the second optical path, preferably more than 5 times the length and still preferably more than 8 times the length.

16. An optical absorption gas analyser according to claim 1 wherein the length of the second optical path which the sample can intercept is less than or equal to 40 mm, preferably less than or equal to 20 mm, still preferably less than or equal to 10 mm.

17. An optical absorption gas analyser according to claim 1 wherein the radiation source assembly comprises a narrow band emitter adapted to emit radiation over a waveband corresponding to an absorption wavelength of the target gas.

18. An optical absorption gas analyser according to claim 17 wherein the width of the waveband emitted by the radiation source assembly is less than or equal to 1 micron.

19. An optical absorption gas analyser according to claim 17 wherein the radiation source assembly comprises a filter for controlling the waveband emitted.

20. An optical absorption gas analyser according to claim 19 wherein the filter is an interference filter.

21. An optical absorption gas analyser according to claim 1 wherein the radiation source assembly comprises an emitter having a response time of less than or equal to 100 milliseconds, preferably less than 1 milliseconds, still preferably less than 50 microseconds.

22. An optical absorption gas analyser according to claim 1 wherein the radiation source assembly comprises a LED.

23. An optical absorption gas analyser according to claim 1 wherein the radiation is infrared radiation.

24. An optical absorption gas analyser according to claim 1 wherein the first and second detector assemblies are adapted to detect radiation of the same wavelength(s) as each other, corresponding to an absorption wavelength of the target gas.

25. An optical absorption gas analyser according to claim 1 where in the first and second detector assemblies each comprise a filter for controlling the wavelength(s) of radiation detected.

26. An optical absorption gas analyser according to claim 1 wherein the first and second detector assemblies each comprise a photodetector, preferably a photodiode, a pyroelectric photodetector or a thermocouple photodetector.

27. An optical absorption gas analyser according to claim 1 further comprising a controller adapted to control power supplied to the radiation source assembly.

28. An optical absorption gas analyser according to claim 27 wherein the controller is adapted to perform pulse width modulation control, supplying the radiation source assembly with discrete pulses of power.

29. An optical absorption gas analyser according to claim 28 wherein the pulses have a duration of between 15 microseconds and 100 milliseconds, preferably approximately 20 microseconds.

30. An optical absorption gas analyser according to claim 28 wherein the pulse width modulated signal has a period of between 100 microseconds and 10 seconds.

31. An optical absorption gas analyser according to claim 28 wherein the pulse width modulated signal has a duty cycle of between 0.01% and 50%, preferably approximately 0.04% to 0.8%.

32. An optical absorption gas analyser according to any of the preceding claims, further comprising a power source, preferably a battery, a solar cell or a solar-powered battery.

33. An optical absorption gas analyser according to claim 1 wherein the first and second detector assemblies are located adjacent one another, preferably arranged on the same or adjacent faces of the chamber.

34. An optical absorption gas analyser according to claim 1 wherein the first and second detector assemblies are arranged in thermal contact with one another.

35. An optical absorption gas analyser according to claim 34 wherein a thermal conductor is connected between the first and second detector assemblies.

36. An optical absorption gas analyser according to claim 34 wherein the first and second detector assemblies are mounted on a thermally conductive plate.

37. An optical absorption gas analyser according to claim 1 wherein the chamber is provided with at least one aperture for gas ingress from the surrounding atmosphere.

38. An optical absorption gas analyser according to claim 1 further comprising a condensation preventor for preventing the condensation of water on optical surfaces forming part of the first and/or second optical paths.

39. An optical absorption gas analyser according to claim 38 wherein the condensation preventor comprises a thermal isolator arranged to thermally isolate the or each optical surface.

40. An optical absorption gas analyser according to claim 39 wherein the thermal isolator forms a substrate upon which the optical surface is supported, preferably a mirror surface.

41. An optical absorption gas analyser according to claim 39 wherein the thermal isolator is formed of a material with low thermal capacity and low thermal conductivity, preferably a polymer, still preferably a polymer foam.

42. An optical absorption gas analyser according to claim 38 wherein the condensation preventor comprises a heater arranged to heat the or each optical surface.

43. An optical absorption gas analyser according to claim 42 wherein the optical surface comprises a conductive material and is provided with connectors for connection to a power supply to thereby form a heating element.

44. An optical absorption gas analyser according to claim 43 further comprising a controller for controlling power supply to the heating element.

45. An optical absorption gas analyser according to claim 43 wherein the optical surface is reflective and comprises a metallic material, preferably aluminium, silver or gold.

* * * * *